United States Patent
Behringer et al.

(10) Patent No.: US 6,512,580 B1
(45) Date of Patent: Jan. 28, 2003

(54) METHOD AND APPARATUS FOR PORTABLE PRODUCT AUTHENTICATION

(75) Inventors: Fredrich Behringer, Old Lyme, CT (US); Sarka Aubrecht, Mystic, CT (US); Richard H. Selinfreund, Guilford, CT (US); Rakesh Vig, Durham, CT (US)

(73) Assignee: Verification Technologies, Inc., Centerbrook, CT (US)

( * ) Notice: Subject to any disclaimer, the term of this patent is extended or adjusted under 35 U.S.C. 154(b) by 0 days.

(21) Appl. No.: 09/428,704

(22) Filed: Oct. 27, 1999

(51) Int. Cl.[7] .............................................. G01N 21/01
(52) U.S. Cl. ..................... 356/244; 436/172; 436/165; 422/101; 422/104
(58) Field of Search ............................... 356/244, 246, 356/432–440; 422/102, 104, 99, 100, 101; 436/164, 165, 172; 250/339.07, 343

(56) References Cited

U.S. PATENT DOCUMENTS

| | | |
|---|---|---|
| 1,822,098 A | 8/1931 | Huntress |
| 2,265,196 A | 12/1941 | Riley |
| 2,521,124 A | 9/1950 | Miller |
| 3,356,462 A | 12/1967 | Cooke et al. |
| 3,412,245 A | 11/1968 | Halverson |
| 3,444,517 A | 5/1969 | Rabinow |
| 3,473,027 A | 10/1969 | Freeman et al. |
| 3,500,047 A | 3/1970 | Berry |
| 3,533,744 A | 10/1970 | Unger |
| 3,591,283 A | 7/1971 | Peisach |
| 3,624,644 A | 11/1971 | Higgins |
| 3,649,464 A | 3/1972 | Freeman |
| 3,662,181 A | 5/1972 | Hercher et al. |
| 3,663,813 A | 5/1972 | Shaw |
| 3,886,083 A | 5/1975 | Laxer |
| 3,928,226 A | 12/1975 | McDonough et al. |

(List continued on next page.)

FOREIGN PATENT DOCUMENTS

| | | |
|---|---|---|
| CH | 654467 A5 | 2/1986 |
| DE | 2 118 928 | 11/1971 |
| DE | 196 17 106 A1 | 10/1997 |
| EP | 0207360 A | 1/1987 |

(List continued on next page.)

OTHER PUBLICATIONS

International Search Report for PCT application No. PCT/US 01/10911, with international filing date of Apr. 4, 2001.
Bruno, A., et al., "All–Solid–State Miniaturized Fluorescence Sensor Array for the Determination of Critical Gases and Electrolytes in Blood," Analytical Chemistry, 60: 507–513, Feb. 1, 1997.

(List continued on next page.)

Primary Examiner—Hoa Q. Pham
(74) Attorney, Agent, or Firm—Wolf, Greenfield & Sacks, P.C.

(57) ABSTRACT

A method and apparatus for on-site verification of product authentication and quality includes a microplate having a substrate with a light-emissive compound thereon. The substrate provides immobilization of the light-emissive compounds and provides a three-dimensional environment similar to free solution for reactions with the product sample to occur. The microplate may include any material having desired light reflective properties and a surface to retain the light-emissive compounds therein. A metered amount of light-emissive compound is placed on the microplate by any desired metering method, such as hand-metering by skilled technicians, automatic metering using robotic equipment, or printing using for example, piezoelectric dispensing technology. In this respect, the light-emissive compound is placed on a microplate, with the microplate. Once the light-emissive compound is applied to the substrate, the microplate may be sent to the test site where product testing is to be performed. A sample product is placed on the microplate and the light-emissive is compound thereon is free to react with key ingredients in the sample product. Light emission from the light-emissive compound and the key ingredient is compared to a fingerprint.

34 Claims, 3 Drawing Sheets

U.S. PATENT DOCUMENTS

| | | | |
|---|---|---|---|
| 3,992,158 A | 11/1976 | Przybylowicz et al. | |
| 3,996,006 A | 12/1976 | Pagano | |
| 4,015,131 A | 3/1977 | McDonough et al. | |
| 4,018,643 A | 4/1977 | Levine | |
| 4,038,151 A | 7/1977 | Fadler et al. | |
| 4,053,433 A | 10/1977 | Lee | |
| 4,077,845 A | 3/1978 | Johnson | |
| 4,078,656 A | 3/1978 | Crane et al. | |
| D248,044 S | 5/1978 | Odom, Jr. et al. | |
| 4,087,332 A | 5/1978 | Hansen | |
| 4,118,280 A | 10/1978 | Charles et al. | |
| 4,146,792 A | 3/1979 | Stenzel et al. | |
| 4,154,795 A | 5/1979 | Thorne | |
| 4,181,500 A | 1/1980 | Cowsar et al. | |
| 4,202,491 A | 5/1980 | Suzuki | |
| 4,235,964 A | 11/1980 | Bochner | |
| 4,243,694 A | 1/1981 | Mansukhani | |
| 4,260,392 A | 4/1981 | Lee | |
| 4,329,317 A | 5/1982 | Detweiler et al. | |
| 4,351,183 A | 9/1982 | Egbert | |
| 4,365,970 A | 12/1982 | Lawrence et al. | |
| 4,382,064 A | 5/1983 | Detweiler et al. | |
| 4,387,112 A | 6/1983 | Blach | |
| 4,439,356 A | 3/1984 | Khanna et al. | |
| 4,450,231 A | 5/1984 | Ozkan | |
| 4,451,521 A | 5/1984 | Kaule et al. | |
| 4,451,530 A | 5/1984 | Kaule et al. | |
| 4,468,410 A | 8/1984 | Zeya | |
| 4,485,308 A | 11/1984 | Rabatin | |
| 4,486,536 A | 12/1984 | Baker et al. | |
| 4,501,496 A | 2/1985 | Griffin | |
| 4,514,085 A | 4/1985 | Kaye | |
| 4,540,595 A | 9/1985 | Acitelli et al. | |
| 4,557,900 A | 12/1985 | Heitzmann | |
| 4,567,370 A | 1/1986 | Falls | |
| 4,589,551 A | 5/1986 | Hellon | |
| 4,589,743 A | 5/1986 | Clegg | |
| 4,598,205 A | 7/1986 | Kaule et al. | |
| 4,620,776 A | 11/1986 | Ima | |
| 4,631,174 A | 12/1986 | Kondo | |
| 4,632,901 A | 12/1986 | Valkirs et al. | |
| 4,642,526 A | 2/1987 | Hopkins | |
| 4,657,540 A | 4/1987 | Iwamoto et al. | |
| 4,736,425 A | 4/1988 | Jalon | |
| 4,746,631 A | 5/1988 | Clagett | |
| 4,756,557 A | 7/1988 | Kaule et al. | |
| 4,767,205 A | 8/1988 | Schwartz et al. | |
| 4,789,804 A | 12/1988 | Karube et al. | |
| 4,806,316 A | 2/1989 | Johnson et al. | |
| 4,818,677 A | 4/1989 | Hay-Kaufman et al. | |
| 4,865,812 A | 9/1989 | Kuntz et al. | |
| 4,882,192 A | 11/1989 | Butland | |
| 4,889,365 A | 12/1989 | Chouinard | |
| 4,897,173 A | 1/1990 | Nankai et al. | |
| 4,916,056 A | 4/1990 | Brown, III et al. | |
| 4,921,280 A | 5/1990 | Jalon | |
| 4,927,180 A | 5/1990 | Trundle et al. | |
| 4,948,442 A | 8/1990 | Manns | |
| 4,966,856 A | 10/1990 | Ito et al. | |
| 4,983,817 A | 1/1991 | Dolash et al. | |
| 5,005,873 A | 4/1991 | West | |
| 5,018,866 A | 5/1991 | Osten | |
| 5,030,421 A | 7/1991 | Muller | |
| 5,030,832 A | 7/1991 | Williams et al. | |
| 5,039,490 A | 8/1991 | Marsoner et al. | |
| 5,039,492 A | 8/1991 | Saaski et al. | |
| 5,047,215 A | 9/1991 | Manns | |
| 5,049,673 A | 9/1991 | Tsien et al. | |
| 5,093,147 A | 3/1992 | Andrus et al. | |
| 5,106,582 A | 4/1992 | Baker | |
| 5,114,676 A | 5/1992 | Leiner et al. | |
| 5,118,349 A | 6/1992 | Jalon | |
| 5,128,243 A | 7/1992 | Potter et al. | |
| 5,128,882 A | 7/1992 | Cooper et al. | |
| 5,130,231 A | 7/1992 | Adams et al. | |
| 5,135,569 A | 8/1992 | Mathias | |
| 5,139,812 A | 8/1992 | Lebacq | |
| 5,147,042 A | 9/1992 | Levy | |
| 5,176,257 A | 1/1993 | Levy | |
| 5,194,289 A | 3/1993 | Butland | |
| 5,200,051 A | 4/1993 | Cozzette et al. | |
| 5,208,630 A | 5/1993 | Goodbrand et al. | |
| 5,246,869 A | 9/1993 | Potter et al. | |
| 5,256,372 A | 10/1993 | Brooks et al. | |
| 5,260,032 A | 11/1993 | Muller | |
| 5,264,103 A | 11/1993 | Yoshioka et al. | |
| 5,272,090 A | 12/1993 | Gavish et al. | |
| 5,279,967 A | 1/1994 | Bode | |
| 5,282,894 A | 2/1994 | Albert et al. | |
| 5,286,286 A | 2/1994 | Winnik et al. | |
| 5,290,705 A * | 3/1994 | Davis | 436/164 |
| 5,292,000 A | 3/1994 | Levy | |
| 5,292,855 A | 3/1994 | Krutak et al. | |
| 5,307,144 A * | 4/1994 | Hiroshi et al. | 356/244 |
| 5,313,264 A | 5/1994 | Ivarsson et al. | |
| 5,319,436 A | 6/1994 | Manns et al. | |
| 5,321,261 A | 6/1994 | Valenta | |
| 5,336,714 A | 8/1994 | Krutak et al. | |
| 5,338,066 A | 8/1994 | Gundjian | |
| 5,338,067 A | 8/1994 | Gundjian | |
| 5,360,628 A | 11/1994 | Butland | |
| 5,366,902 A | 11/1994 | Cox et al. | |
| 5,409,583 A | 4/1995 | Yoshioka et al. | |
| 5,409,666 A | 4/1995 | Nagel et al. | |
| 5,418,136 A | 5/1995 | Miller et al. | |
| 5,418,855 A | 5/1995 | Liang et al. | |
| 5,421,869 A | 6/1995 | Gundjian et al. | |
| 5,424,959 A | 6/1995 | Reves et al. | |
| 5,429,952 A | 7/1995 | Garner et al. | |
| 5,438,403 A | 8/1995 | Hoshino et al. | |
| 5,450,190 A | 9/1995 | Schwartz et al. | |
| 5,457,527 A | 10/1995 | Manns et al. | |
| 5,468,650 A | 11/1995 | Skov et al. | |
| 5,494,638 A | 2/1996 | Gullick | |
| 5,496,701 A | 3/1996 | Pollard-Knight | |
| 5,498,549 A | 3/1996 | Nagel et al. | |
| 5,512,490 A * | 4/1996 | Walt et al. | 436/171 |
| 5,516,362 A | 5/1996 | Gundjian et al. | |
| 5,519,218 A * | 5/1996 | Chang | 250/339.07 |
| 5,521,984 A | 5/1996 | Denenberg et al. | |
| 5,525,516 A | 6/1996 | Krutak et al. | |
| 5,545,567 A | 8/1996 | Gretillat et al. | |
| 5,546,471 A | 8/1996 | Merjanian | |
| 5,547,501 A | 8/1996 | Maruyama et al. | |
| 5,568,177 A | 10/1996 | Talvalkar et al. | |
| 5,569,317 A | 10/1996 | Sarada et al. | |
| 5,574,790 A | 11/1996 | Liang et al. | |
| 5,582,697 A | 12/1996 | Ikeda et al. | |
| 5,589,350 A | 12/1996 | Bochner | |
| 5,599,578 A | 2/1997 | Butland | |
| 5,608,225 A | 3/1997 | Kamimura et al. | |
| 5,611,433 A | 3/1997 | Levy | |
| 5,614,008 A | 3/1997 | Escano et al. | |
| 5,618,682 A | 4/1997 | Scheirer | |
| 5,625,706 A | 4/1997 | Lee et al. | |
| 5,631,170 A | 5/1997 | Attridge | |
| 5,632,959 A | 5/1997 | Mohajer | |
| 5,641,640 A | 6/1997 | Hanning | |
| 5,650,062 A | 7/1997 | Ikeda et al. | |
| 5,651,869 A | 7/1997 | Yoshioka et al. | |
| 5,665,151 A | 9/1997 | Escano et al. | |

| | | |
|---|---|---|
| 5,671,288 A | 9/1997 | Wilhelm |
| 5,673,338 A | 9/1997 | Denenberg et al. |
| 5,710,626 A | 1/1998 | O'Rourke et al. |
| 5,711,915 A | 1/1998 | Siegmund et al. |
| 5,716,825 A | 2/1998 | Hancock et al. |
| 5,719,948 A | 2/1998 | Liang |
| 5,723,341 A * | 3/1998 | Truett .................... 436/171 |
| 5,728,350 A | 3/1998 | Kinoshita et al. |
| 5,736,342 A | 4/1998 | Van Wie et al. |
| 5,753,511 A | 5/1998 | Selinfreund |
| 5,762,873 A | 6/1998 | Fanning et al. |
| 5,764,355 A * | 6/1998 | Gagnon et al. .......... 356/244 |
| 5,773,808 A | 6/1998 | Laser |
| 5,774,160 A | 6/1998 | Gundjian |
| 5,776,713 A | 7/1998 | Garner et al. |
| 5,784,193 A | 7/1998 | Ferguson |
| 5,786,182 A | 7/1998 | Catanzariti et al. |
| 5,786,509 A | 7/1998 | Belding et al. |
| 5,800,785 A | 9/1998 | Bochner |
| 5,807,625 A | 9/1998 | Amon et al. |
| 5,811,152 A | 9/1998 | Cleary |
| 5,818,582 A | 10/1998 | Fernandez et al. |
| 5,822,473 A | 10/1998 | Magel et al. |
| 5,837,042 A | 11/1998 | Lent et al. |
| 5,851,489 A | 12/1998 | Wolf |
| 5,856,174 A | 1/1999 | Lipshutz et al. |
| 5,861,618 A | 1/1999 | Berson |
| 5,867,586 A | 2/1999 | Liang |
| 5,874,219 A | 2/1999 | Rava et al. |
| 5,879,951 A | 3/1999 | Sy |
| 5,919,712 A | 7/1999 | Herron et al. |
| 5,922,188 A | 7/1999 | Ikeda et al. |
| 5,922,550 A | 7/1999 | Everhart et al. |
| 5,922,591 A | 7/1999 | Anderson et al. |
| 5,922,594 A | 7/1999 | Läfås |
| 5,923,413 A | 7/1999 | Laskowski |
| 5,927,547 A | 7/1999 | Papen et al. |
| 5,939,024 A | 8/1999 | Robertson |
| D414,272 S | 9/1999 | O'Bear et al. |
| 5,955,352 A | 9/1999 | Inoue et al. |
| 5,955,729 A | 9/1999 | Nelson et al. |
| 5,961,926 A | 10/1999 | Kolb et al. |
| 5,966,205 A | 10/1999 | Jung et al. |
| 5,989,835 A | 11/1999 | Dunlay et al. |
| 5,998,128 A | 12/1999 | Roelant |
| 6,001,573 A | 12/1999 | Roelant |
| 6,015,715 A | 1/2000 | Kirschner et al. |
| 6,063,339 A * | 5/2000 | Tisone et al. ............ 422/67 |
| 6,232,124 B1 | 5/2001 | Selinfreund |
| 6,280,690 B1 * | 8/2001 | Tadion .................... 422/102 |

FOREIGN PATENT DOCUMENTS

| | | |
|---|---|---|
| EP | 0327163 | 9/1989 |
| EP | 0354204 B1 | 5/1992 |
| EP | 0589991 B1 | 4/1994 |
| EP | 0591315 B1 | 4/1994 |
| EP | 0653635 A1 | 5/1995 |
| EP | 0 736 767 A1 | 10/1996 |
| EP | 0878537 A1 | 11/1998 |
| GB | 1 334 866 | 1/1974 |
| GB | 1485506 A | 9/1977 |
| GB | 2 258 528 A | 2/1993 |
| GB | 2298713 B | 9/1996 |
| GB | 2 334 574 A | 8/1999 |
| JP | 63184039 | 7/1988 |
| WO | WO9506249 | 2/1995 |
| WO | WO96 37768 A | 11/1996 |
| WO | WO 97131332 | 8/1997 |
| WO | WO99/54714 A1 | 10/1999 |
| WO | WO01/31341 A1 | 5/2001 |

OTHER PUBLICATIONS

AOAC Official Methods of Analysis, 1990, pp. 752–754.

Barrett, "Molecular Fingerprinting of Food Bourne Pathogens," CDD IFT Symposium, Jun. 21–22, 1996.

Bock, G., et al., "Photometric Analysis of Antifading Reagents for Immunofluorescence with Laser and Conventional Illumination Sources," Journal of Histochemistry and Cytochemistry, 33:699–705 (1985).

Chan, et al., Biochem, Biophys, Acta, vol. 204, p. 252, 1970.

Constant, et al., ACS Abstract, Issue of Chemical and Engineering News, Aug. 25, 1994.

Coons, et al., J. Exp. Med., vol. 91, pp. 1–14, 1950.

Crossley et al., Journal of the Chemical Society, Perkin Transactions 2, 1615 (1994).

Dragoco Report, pp. 12–13, 1990.

Furomoto et al., IEEE, J. Quantum Electron, QE–6, 262 (1970).

Gill, D., "Inhibition of fading in fluorescence microscopy of fixed cells," Dept. of Physics, Ben Gurion University, Israel (Jul. 1978).

Huff, J., "Enhancement of Specific Immunofluorescent Findings with Use of a Para–Phenylenediamine Mounting Buffer," Journal of Investigative Dermatology, 78: 449–450 (1982).

Iatridou, H., Cell Calcium, vol. 15, pp. 190–198, 1994.

Johnson, G.D., et al., "Fading of Immunofluorescence during Microscopy: a Study of the Phenomenon and its Remedy," Journal of Immunological Methods, 55: 231–242 (1982).

Johnson, G.D., et al., "A Simple Method of Reducing the Fading of Immunofluorescence During Microscopy," Journal of Immunological Methods, 43: 349–350 (1981).

Larsen, R., et al., "Spectroscopic and Molecular Modeling Studies of Caffeine Complexes with DNA Intercalators, "Biophysical Journal, 70:443–452 (Jan. 1996).

Lee, S.P., et al., "A Fluorometric Assay for DNA Cleavage Reactions Characterized with BamHl Restriction Endonuclease," Analytical Biochemistry, 220:377–383 (1994).

Platt, J. L. et al., "Retardation of Fading and Enhancement of Intensity of Immunofluorescence by p–Phenylenediamine," Journal of Histochemistry and Cytochemistry, 31:840–842 (1983).

Practical Fluorescence, Second Edition, G.G. Guilbault, Editor, Marcel Dekker, Inc., p. 32, 1990.

Raybourne, "Flow Cytometry in Food Microbiolog," IFT Symposiun FDA, Jun. 21–22, 1996.

Stryer, L., "Fluorescence Energy Transfer as a Spectroscopic Ruler," Ann. Rev. Biochem., 47:819–46 (1978).

Uchiyama, H., et al., "Detection of Undegraded Oligonucleotides in Vivo Fluorescence Resonance Energy Transfer," Journal of Biological Chemistry, 271: 380–384, Jan. 1996).

Wittwer, C.T., et al. "Continuous Fluorescence Monitoring of Rapid Cycle DNA Amplification," BioTechniques, 22:130–138 (Jan. 1997).

Biocode product literature, "Covert Product Identification".

Freemantle, M., "Downsizing Chemistry: Chemical analysis and synthesis on micriships promise a variety of potential benefits", C&EN London, pp. 27–36, Feb. 22, 1999.

Furneaux, R.C., et al., "The formation of controlled–porosity membranes from anodically oxidized aluminum", Nature, vol. 337, No. 6203, pp. 147–149, Jan. 12, 1989.

Schauer, C.L., et al., "Cross–reactive optical sensor arrays", ACS Meetings, San Francisco National Meeting, Downloaded from http://schedule.acs.org/cgi–bin/ACS/perso . . . , Mar. 7, 2000.

Skolnick, A., "Russian and US Researchers Develop 'Biochips' for Faster, Inexpensive Biomedical Tests", JAMA, vol. 275, No. 8, pp. 581–582, Feb. 28, 1996.

Stanley, D., "UT scientists engineer a tiny arbiter of taste", Austin American Statesman Newspaper, p. B1, Jul. 26, 1998.

Stringer, "Photonics Center launches three new companies", Mass. High Tech., p. 11, Apr. 26–May 2, 1999.

Biacore Website, "Sensor chips for BIACORE analysis systems", downloaded from webmaster.bia@eu.biacore.com; undated.

Biacore Website, "Principles of BIAtechnology", downloaded from webmaster.bia@eu.biacore.com, Undated.

Biacore Website, "protein binding", downloaded from webmaster.bia@eu.biacore.com, undated.

Biodiscovery website, "Inventing Expression Bioinformatics", undated.

Cambridge Healthtech Institute Website, downloaded from www.healthtech.com, undated.

Corning Microarray Technology Website, "CMT–GAPS Coated Slides—FAQ's", downloaded from www.cmt.corning.com/dev/company_info/who/techno . . ., Oct. 26, 1999.

Packard Website, "The Biochip Arrayer", Downloaded from www.packardinst.com/prod_serv/–Biochiparrayer.htm, Oct. 26, 1999.

Glabe et al., Anal. Biochem, 130:287–294 (1983).

Minta et al., J. Biol. Chem. 264:8171, 1989.

Eric V. Anslyn, et al. "Rapid and Efficient Analysis of Multiple Chemical/Biochemical Agents in Solution Using Sensor Arrays: Toward the Development of an Electronic Tongue," The University of Texas at Austin.

Junior LB 9509, the portable luminometer:, downloaded from http://www.berthold.com.au/bioanalytical_pages/LB9509.html, downloaded Oct. 26, 1999.

The Invisible Barcode, downloaded from http://www.canadianpackaging.com/C . . . aging, downloaded Jul. 1999.

1st Advanced Packaging Technology Conference held Nov. 9–11, 1998, downloaded from http://auburn.main.com/tse/imi/completed/advanced–pkg–euro.html; downloaded Jul. 1999.

Phosphor Technology, downloaded from http:/www.phosphor.demon.co.uk/iruv.htm; downloaded Jul. 1999.

Fluorescent Inks downloaded from http://www.uvp.com/html/inks.html; downloaded Jul. 1999.

V.L. Engineering, Our Products; downloaded from http://www.vlengineering.com/products/wizard_PV6A Downloaded July 1999.

R. Service, Microchip Arrays Put DNA on the Spot, Oct. 16, 1998, vol. 282 Science, pp. 396–399.

R. Service, Coming Soon: The Pocket DNA Sequencer, Oct. 16, 1998, vol. 282, Science, pp. 399–401. 402.

I. Amato, Fomenting a Revolution, in Miniature, Oct. 16, 1998, vol. 282, Science, pp. 402–404.

Web Site Disclosure: Packard Instrument Company: Tools for Life Science Research, pp. 1–2.

* cited by examiner

METHOD AND APPARATUS FOR PORTABLE PRODUCT AUTHENTICATION

FIELD OF THE INVENTION

This invention relates generally to methods and apparatuses for authenticating a sample product, and more specifically, to methods and apparatuses for providing light-emissive compounds for use with product authentication equipment.

BACKGROUND OF THE INVENTION

Authenticating and monitoring products to discriminate between very similar complex mixtures is useful for various reasons. For example, the use of counterfeit substances (e.g., misbranded product from a competitor or misformulated product from a licensee/franchisee) should be detected to preserve the integrity of a brand. Also, low quality substances (e.g., diluted or misformulated product) should be quickly and conveniently detected for appropriate correction.

One particular industry that could benefit from such authenticity testing and monitoring is the beverage industry. With respect to monitoring production of the beverage, a simple, quick and product specific at-line test to determine whether the beverages being produced are within specification is desirable. Typically, the beverages are being bottled at a rate of 2000 bottles/minute. Therefore, standard off-line analytical techniques for monitoring product quality, such as GC/MS or HPLC, are complex and time consuming in that the beverages that are being tested have already been introduced to the market. A desirable monitoring procedure should provide relatively instant response time, be usable by non-scientific personnel, be accurate (e.g., having an error rate of less that 2.5%) and survive harsh plant environments.

With respect to product authentication, an example of an industry that could benefit is the beer industry. For example, at-line testing allows a determination as to whether a particular tap at a pub was actually serving authentic beer, without being sensitive to batch-to-batch variability of the a particular brand. Similarly, detection of dilution of a product may be important to the distilled spirits industry.

Commonly assigned U.S. Pat. No. 5,753,511, which is herein incorporated by reference in its entirety, discloses an automated method of developing a database to store information for "fingerprint"-type analysis of products (even as to product lot numbers and batch). The automated analysis is a method of evaluating and discriminating products, even within a narrow field or industry, competing and otherwise, to establish authenticity or point of origin of the product. The invention therein relates to an automated method for identifying key ingredients and/or the relative amounts of key ingredients in products mixed with light-emissive compounds. Scanning for light emission of a predetermined wavelength when the sample product is mixed with the light-emissive compound is used when comparing the sample product to a fingerprint.

The laboratory equipment used to authenticate the sample referred to in '511 is not easily and cost effectively transported. Thus, determining product authenticity on site, either at manufacturing points, at distribution points, or at consumption points is impractical.

Co-pending U.S. patent application Ser. No. 09/232,324, assigned to the present assignee and herein incorporated by reference in its entirety, discloses a portable product authentication device and a method of authenticating products. One embodiment disclosed therein requires a proper mixing of both the light-emissive compound and sample product prior to testing the sample for product authenticity. Although effective, mixing of the sample product and the light-emissive compound on-site can be cumbersome and time-consuming and may require a certain skill level.

In another embodiment disclosed in application '324, the light-emissive compound may be formed on a chip and the chip, together with a small amount of sample, is placed in the authentication device to determine the authenticity of the product. As discussed therein, the light-emissive compound may be attached to the chips through any physical or chemical means including covalent and non-covalent bonding. For example, the light-emissive may be dissolved in a solvent, then applied at a preselected concentration to the surface of the chip.

The solvent is then evaporated away, leaving the light-emissive compound non-covalently attached to the surface of the chip. Although this results in a simple solution to providing light-emissive compounds without requiring mixing, the resulting chip may be costly and susceptible to damage.

To overcome this particular disadvantage, also disclosed in '324, the light-emissive compound may be covalently attached to the surface of the chip. In this instance, the light-emissive compound may have groups reactive under appropriate conditions with groups on the surface of the chip, which may be reactive groups of the chip per se, or may be linker molecules attached to the surface of the chip. Such cross-linking, however, often requires a labor intensive process, resulting in a costly product. In addition, the cross-linking molecules may interfere with a proper reading of the light emission. For example, current microarray technology teaches the art of immobilizing chemistry for the detection of DNA specific or protein specific sequences. The amino-silane surface chemistry allows a fixed molecule to bind products for applied genomic gene expression studies and medical diagnostic information. The inventors of the present invention have found that adopting such technology for use in binding light-emissive compounds met with limited success.

Another example of providing light-emissive compounds is disclosed in co-pending U.S. patent application Ser. No. 09/173,814, assigned to the present assignee and herein incorporated by reference in its entirety, wherein a microplate may be used in place of the above-mentioned chip. As disclosed therein, the microplate includes a plurality of wells formed in the surface of the microplate. Light-emissive compounds are placed in the wells and attached thereto by directly bonding to the surface or through the use of a linker molecule or incorporated into the matrix created by the base material of the microplate itself. In addition, the invention therein describes the use of a dried light-emissive compound on the microplate or the microplate is packaged.

What is therefore needed is a simple, low cost method and apparatus that provides light-emissive compounds for reaction with a sample product in an environment that is or simulates a liquid solution and that provides the ability for authenticity testing and monitoring of sample product at-line.

SUMMARY OF THE INVENTION

The present invention features a method and apparatus for on-site verification of product authentication and quality. A microplate having a substrate includes a light-emissive compound thereon. The substrate provides immobilization of the light-emissive compounds and provides a three-dimensional environment similar to free solution for reactions with the product sample to occur. The microplate may include any material having desired light reflective properties and a surface to retain the light-emissive compounds therein. A metered amount of light-emissive compound is placed on the microplate by any desired metering method, such as hand-metering by skilled technicians, automatic metering using robotic equipment, or printing using for example, piezoelectric dispensing technology. Once the light-emissive compound is applied to the substrate, the microplate may be sent to the test site where product testing is to be performed. A sample product is placed on the microplate and the light-emissive compound thereon is free to react with key ingredients in the sample product. Light emission from the light-emissive compound and the key ingredient is compared to a fingerprint.

In one illustrative embodiment of the invention, a microplate is provided. The microplate includes a solid base and a porous substrate layered on the base. At least one light-emissive compound is absorbed in the substrate in a manner to allow a sample placed on the microplate to react with the at least one light-emissive compound.

In another illustrative embodiment of the invention, a microplate is provided. The microplate includes a solid base having a top wall. At least one well is integral with and opens into the top wall. The at least one well defines an inner surface. At least one light-emissive compound is deposited into the at least one well to allow a sample placed on the microplate to react with the at least one light-emissive compound in the well. A semi-permeable membrane is formed over the at least one well. The semi-permeable membrane is adapted to allow the sample to permeate from outside the at least one well into the at least one well while retaining the at least one light-emissive compound within the at least one well.

In yet another illustrative embodiment of the invention, a microplate is provided. The microplate includes a solid base and at least one light-emissive compound held to the base to allow a sample placed on the microplate to react with the at least one light-emissive compound. A barrier is formed on the base and is adapted to transfer a desired portion of the sample to the at least one light-emissive compound while holding the at least one light-emissive compound to the base.

In still another illustrative embodiment of the invention, a system for verifying authenticity of a sample product is provided. The system includes a microplate and a product authentication device for reading the microplate. The microplate includes a solid base and a porous substrate layered on the base. At least one light-emissive compound is absorbed in the substrate to allow a sample placed on the microplate to react with the at least one light-emissive compound. The authentication device includes a light source for irradiating the microplate with a predetermined wavelength of light, an optical detector for detecting at least one emitted wavelength of light generated by the sample in response to the irradiating wavelength of light to provide a sample characteristic, and a controller coupled to the optical detector for receiving the sample characteristic and comparing the sample characteristic to a fingerprint.

In another illustrative embodiment of the invention, a system for verifying authenticity of a sample product is provided. The system includes a microplate and a product authentication device for reading the microplate. The microplate includes a solid base and a top wall and at least one well integral with and opening into the top wall. The at least one well defines an inner surface. At least one light-emissive compound is deposited into the at least one well to allow a sample placed on the microplate to react with the at least one light-emissive compound in the well. A semi-permeable membrane is formed over the at least one well. The semi-permeable membrane is adapted to allow the sample placed on the microplate to permeate from outside the at least one well into the at least one well while retaining the at least one light-emissive compound within the at least one well. The authentication device includes a light source for irradiating the microplate with a predetermined wavelength of light, an optical detector for detecting at least one emitted wavelength of light generated by the sample in response to the irradiating wavelength of light to provide a sample characteristic, and a controller coupled to the optical detector for receiving the sample characteristic and comparing the sample characteristic to a fingerprint.

In yet another illustrative embodiment of the invention, a system for verifying authenticity of a sample product is provided. The system includes a microplate and a product authentication device for reading the microplate. The microplate includes a solid base and at least one light-emissive compound held to the base. A barrier is formed on the base and is adapted to transfer a desired portion of sample placed on the microplate to the at least one light-emissive compound while holding the at least one light-emissive compound to the base. The authentication device includes a light source for irradiating the microplate with a predetermined wavelength of light, an optical detector for detecting at least one emitted wavelength of light generated by the sample in response to the irradiating wavelength of light to provide a sample characteristic, and a controller coupled to the optical detector for receiving the sample characteristic and comparing the sample characteristic to a fingerprint.

In yet another illustrative embodiment of the invention, a method of providing a light-emissive compound on a microplate is provided. The microplate has a substrate. The method includes the steps of selecting a substrate capable of absorbing at least one light-emissive compound thereon and depositing the at least one light-emissive compound on the substrate using a piezoelectric dispenser.

In still another illustrative embodiment of the invention a method of verifying authenticity of a sample product is provided. The method includes the steps of providing a microplate base having at least one light-emissive compound disposed thereon, applying a sample product to a microplate, irradiating the microplate with a predetermined wavelength of light, detecting at least one emitted wavelength of light generated by the sample in response to the irradiating wavelength of light to provide a sample characteristic, and comparing the sample characteristic to a fingerprint. The microplate has a solid base and a porous substrate layered on the base. The at least one light-emissive compound is absorbed in the substrate. Alternatively, at least one well integral with and opening into the top wall of the base may be provided. The at least one light-emissive compound is deposited into the at least one well. The at least one well has a semi-permeable membrane formed thereover. The semi-permeable membrane is adapted to allow the sample placed on the microplate to permeate from outside the at least one well into the at least one well while retaining the at least one light-emissive compound within the at least one well.

In another illustrative embodiment, a method of verifying authenticity of a sample product is provided. The method includes the steps of providing at least 500 micropores containing a dry light-emissive compound, absorbing a liquid sample into the micropores to permit the sample to solublize and interact with the light-emissive compound in the micropores, irradiating the micropores with a predetermined wavelength of light, detecting at least one emitted wavelength of light generated by the sample in response to the irradiating wavelength of light to provide a sample characteristic, and comparing the sample characteristic to a fingerprint.

Various embodiments of the present invention provide certain advantages and overcome certain drawbacks of the conventional techniques. Not all embodiments of the invention share the same advantages and those that do may not share them under all circumstances. This being said, the present invention provides numerous advantages including the noted advantage of providing light-emissive compounds on a substrate so that the compound and substrate may be used with product authentication equipment.

Further features and advantages of the present invention, as well as the structure and operation of various embodiments of the present invention are described in detail below with reference to the accompanying drawings.

BRIEF DESCRIPTION OF THE DRAWINGS

The invention will now be described, by way of example, with reference to the accompanying drawings, in which.

DETAILED DESCRIPTION

The invention features a microplate for use with a portable product authentication device. The microplate is used in conjunction with a product sample to be tested, analyzing key ingredients or analytes in the product. Light-emissive compounds can be used to identify the product sample. In one aspect, the light-emissive compound is provided on a microplate in a manner that allows the light-emissive compound to freely react with a product sample when a product sample is placed thereon. In this respect, the light-emissive compound is placed on a microplate, with the microplate causing immobilization of the light-emissive compounds and providing a three-dimensional environment similar to free solution for reactions with the product sample to occur. The light-emissive compound together with the product sample is then irradiated using a light source to cause the light-emissive compounds to emit light. The emitted light is then read by an optical detector and then is compared to a stored fingerprint to determine whether the product sample is authentic. Specifically, the emitted properties are compared to a standard fingerprint to determine authenticity. It is to be appreciated that the term "authentic", or any derivative thereof, means an identification as being genuine or without adulteration or identification of point of origin or other desired information.

Light-emissive compounds emit light in response to irradiation with light. Light-emission can be a result of phosphorescence, chemiluminescence or more preferably fluorescence. Specifically, the term "light-emissive compounds", as used herein, means compounds that have one or more of the following properties: 1) they are fluorescent, phosphorescence or luminescent; 2) react, or interact, with components of the sample or the standard or both to yield at least one fluorescent, phosphorescence, or luminescent compound; or 3) react, interact, with at least one fluorescent, phosphorescence, or luminescent compound in the sample product, the standard, or both to alter emission at the emission wavelength.

The term "fingerprint" as used herein, means light emission intensity and/or intensity decay from one or more light-emissive compound in combination with a standard (e.g., authentic) product. Accordingly, each product can have a particular fingerprint.

The term "fingerprint emission profile" as used herein, means an assembly of fingerprints of a standard in combination with a series (or profile) of different light-emissive compounds.

The term "sample characteristic" as used herein refers to light emission quantity or intensity and/or intensity decay or change in quantity from one or more light-emissive compounds in combination with the sample product.

Figure 1:
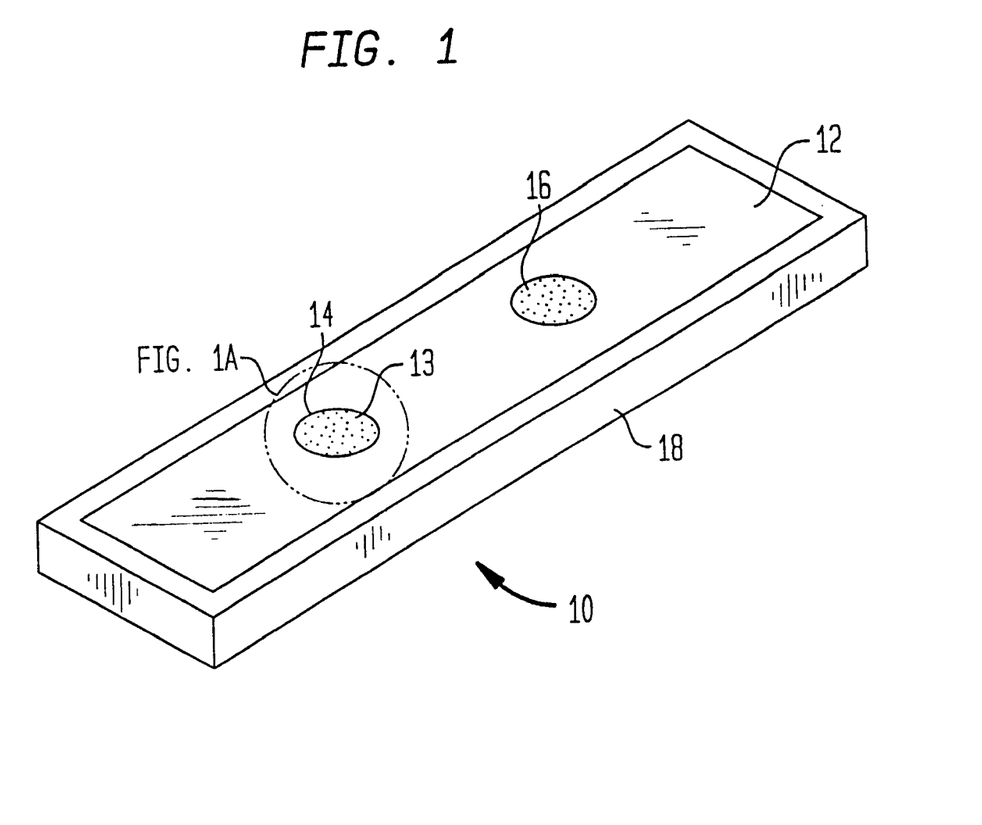
FIG. 1 is a perspective view of one embodiment of an authenticating compound disposed on a substrate.

As shown in FIG. 1, a microplate 10 includes a substrate 12 layered thereon for receiving at least one light-emissive compound 13 in areas located at 14, 16. The light-emissive compound may be applied to the substrate in a suitably metered amount. One (or up to 100 or more) light emissive compound(s) may be applied to the microplate in a manner that allows interaction or a combination of interactions with one or more analyte(s) (key ingredient(s)) in a sample.

Preferably, the microplate also includes a solid base 18 for supporting the substrate 12. The base may be any suitable material having suitable properties such that the combination of the base and the substrate, when the microplate is used in connection with a device having a light source and an optical detector, as will be further described hereinafter, does not interfere with the measurements taken by the device. Preferably, the base is glass. Also, preferably the base is flat.

Substrate 12 is preferably a porous material having 500 or more micropores such that the light-emissive compound may be absorbed in the substrate in a manner to allow the sample, when placed on the substrate, to react with the light-emissive compound. Porous substrates permit immobilization of the light-emissive compounds, and can provide a three-dimensional environment similar to free solution for reactions with the product sample to occur. Furthermore, capillary forces in these substrates cause wicking of liquid from a contact dispenser, resulting in undesirable spread of light-emissive compounds in the substrate. To control such spread, and for other advantages, piezoelectric non-contact dispensing may be used. Piezoelectric dispensing delivers a small, precisely controlled volume, which will be absorbed into the matrix in a consistent manner.

Piezoelectric dispensing technology is based on capillary dispensers which are able to aspirate solutions, such as light-emissive compounds, from source wells and dispense many droplets to destinations in microarray formats. The dispenser consists of a glass capillary which has an orifice of approximately 75 $\mu$m at one end and a connection to a precision syringe pump at the other end. The syringe pump applies vacuum to aspirate solutions through the tip. A piezoelectric transducer around the center of the capillary exerts pressure on the capillary when activated by an electronic pulse to create a pressure wave in the capillary which ejects a droplet of about 350 pL from the orifice, and the end of the capillary refills from the reservoir of system fluid by capillary flow. An example of such a dispenser is the BioChip Arrayer™, available from Packard Instrument Company, Meriden, Conn. USA. Other dispensers may be available from ink jet manufacturers.

In one particular example, the substrate 12 may be formed of silica and preferably a plurality of silica particles. However, it should be appreciate that the present invention is not limited in this respect and that other suitable materials may be used, for example, quartz, etc. Alternatively, if a glass base is used, the glass may be etched such that the etched surface provides a suitable substrate. In this respect, the microplate 10 may be a microplate produced by thin layer chromatography, as is known to those of ordinary skill in the art and which is commercially available from Merck of Darmstadt, Germany. Preferably, the silica particles have a size less than about 25 $\mu$m and can total 500 or more to provide 500 or more micropores, although more or less may be provided.

In this regard, by applying the light-emissive compound to such a substrate, the light-emissive compound may be held thereon without covalently bonding or linking the light-emissive compound to the substrate. In addition, the light-emissive compound may be allowed to dry onto the substrate yet the substrate provides a medium to simulate a liquid environment. Accordingly, although not required, the dried light-emissive compound on the microplate may be suitable for package and transportation to a test sight. If the light-emissive compound is allowed to dry on the substrate, then application of the product sample, when in liquid form, causes the light-emissive compound to enter a liquid solution.

The substrate 12 may also be formed of a membrane. Examples of such membranes include nylon, nitrocellulose and Anapore™. Nylon and nitrocellulose membranes mounted on microscope slides are commercially available from Schleicher and Schuell and Anaporem membranes are available from Whatman (Anadisk Cat#6809-6022), United Kingdom. Compared to non-porous surfaces, conventional nitrocellulose or nylon blotting or transfer membranes have a much larger area available for surface interactions per unit of macroscopic area. Furthermore, a liquid, such as the light-emissive compound and/or the sample product, dispensed onto these membranes will immediately distribute in the membrane by capillary flow, which may result in a relatively uniform distribution.

Anaporerm is an inorganic microporous membrane with a highly controlled, uniform capillary pore structure. It is 60 $\mu$m thick and is available with 200 nm capillary pores which afford the membrane with a great surface area for the immobilization of the light-emissive compounds. The light-emissive compounds can more readily be applied to the membrane using piezoelectric dispensing if the membrane is mounted to a base.

Alternatively, the substrate may be a gel, such as a polyacrylamide gel. Polyacrylamide gel provides a substrate for permitting the immobilization of light-emissive compounds within a three-dimensional matrix. Relatively large amounts of light-emissive compounds per unit area of the microplate can be achieved while avoiding the crowding which may occur on planar surfaces. Compared to a planar surface, the polyacrylamide gels more closely approximates solution conditions. However, the gel restricts the size of molecules forming the light-emissive compound as well as the sample product that can diffuse into the gel.

According to one illustrative embodiment, more than one light-emissive compound may be applied to the substrate. In some instances, it may be desirable to apply at least two light-emissive compounds in a manner such that the compounds are interleaved with each other. That is, the light-emissive compounds are placed on the slide in a manner so as to be adjacent each other. In this respect, the interleaving allows for the production of more than one wavelength of light in a relatively small space. In addition, the interleaving provides significant advantages by dampening background signals while providing the ability to apply ratiometrics as will be described hereinafter.

As shown in FIG. 1, the light-emissive compound is disposed over a selected macroarea 14 of the microplate. Within the macroarea 14, the light-emissive compounds may be placed on the substrate in a format such that a plurality of spaced-apart microareas are provided. This is shown in greater detail in FIG. 1A, wherein the macroarea 14 comprises a plurality of microareas 20.

Figure 1A:
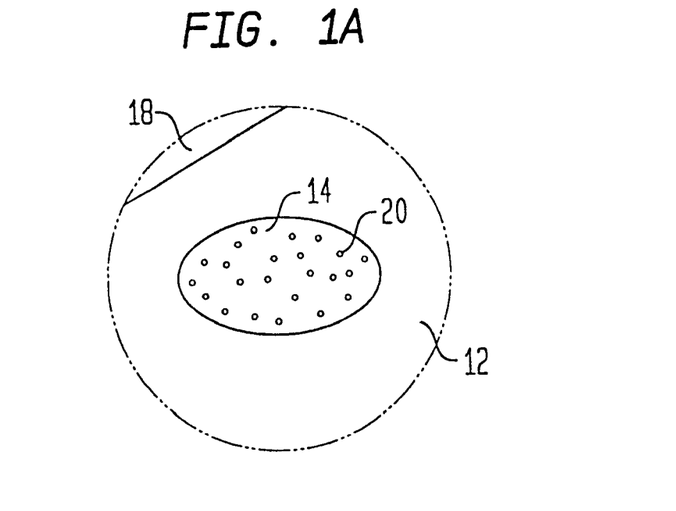
FIG. 1A is enlarged view of the area encircled by line 1A of FIG. 1.

In addition, the macroarea may be split into two or more macroareas, 14, 16, which may be spaced apart from each other. However, it should be appreciated that the present invention is not limited in this respect and that the two or more macroareas may be disposed adjacent each other. In one embodiment (not shown), each macroarea is shaped as a square having an edge with a length of about 6.67 mm. Preferably, four such square macroareas are placed adjacent each other in a line running parallel to the longitudinal axis of the microplate. Each such macroarea may contain one or more light-emissive compounds.

Figure 2:
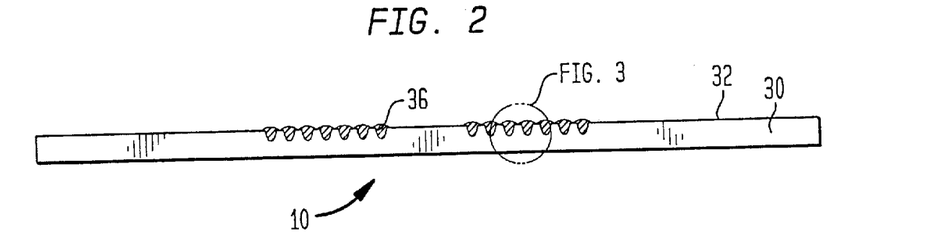
FIG. 2 is a side view of an alternative embodiment of an authenticating compound disposed on a substrate.
Figure 3:
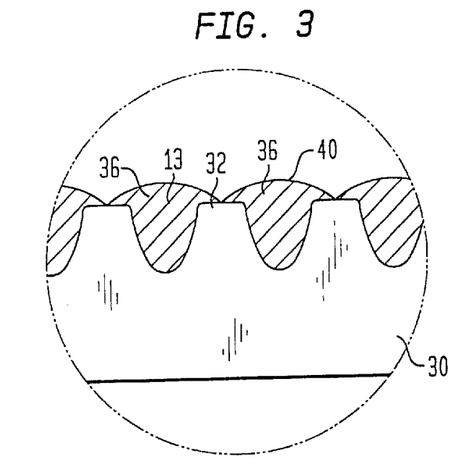
FIG. 3 is an enlarged view of the area encircled by line 3 of FIG. 2.

Turning now to FIGS. 2 and 3, the microplate alternatively may include a base 30 having a top wall 32 and at least one well 34 integral with the top wall 32. The well defines an inner surface 36. A light-emissive compound 13 may be deposited into the well 36. In this embodiment, a semi-permeable membrane 40 may be attached to the top wall 32 so as to encapsulate the light-emissive compound 13 within the well 36. Thus, the semi-permeable membrane acts to hold the light-emissive compound within the well. In this regard, the light-emissive compounds may be in a liquid form. According to one aspect of the present invention, the semi-permeable membrane is adapted to transfer at least a desired portion of the sample to be placed on the microplate to the light-emissive compound within the well. Thus by encapsulating the light-emissive compound within the well, the need to covalently link or bond the light-emissive compound to the microplate is obviated while retaining the desired result of providing the light-emissive compound in liquid form.

As discussed with reference to FIG. 1, adjacent light-emissive compounds may be applied to the microplate. In this regard, more than one well is provided in the microplate. At least one light-emissive compound is deposited into the first well 42, and at least one light-emissive compound is deposited into the second well 44. Preferably, although not required, the light-emissive compounds in each well is different. In addition, although not required, the first and second wells are adjacent each other. Further, the plurality of wells may be disposed over a selected macroarea 42 of the microplate. In addition, the selected macroarea may include first 42 and second 44 spaced apart selected macroareas.

The inventors have found that incorporating a barrier material onto the microplate allows for ready authentication of carbonated beverages. In this respect, in the embodiment described with respect to FIG. 1, the silica or the gel acts to allow the product sample to penetrate through the substrate and react with the light-emissive compound without allowing the larger gas bubbles to also penetrate. Otherwise erroneous readings may occur when attempting to detect emitted wavelength from the reaction of the light-emissive compound with the key ingredient in the sample product when such gas bubbles are present.

Similarly, with respect to FIG. 3, the membrane 40 is sufficient to allow passage of liquid molecules from the sample product to be tested while preventing the gas bubbles from a carbonated beverage to penetrate into the well. The membrane 40 also retains light-emissive compound within the well.

In prior attempts, especially when using the process described in the '511 patent, the sample product to be tested must be diluted in a manner so as to reduce the level of carbonation such that the gas bubbles will not interfere with the proper reaction and reading of the light-emissive compound together with the key ingredient of the sample products. The barrier configuration described herein, obviates this.

Figure 4:
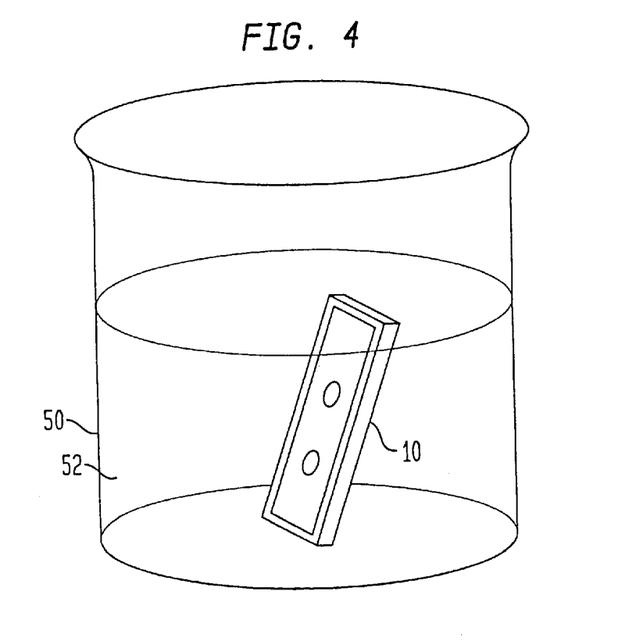
FIG. 4 is a perspective view of an authenticating compound with substrate interacting with a product sample.

Thus, according to one aspect of the present invention, the sample product in its commercial state may be directly applied to the microplate. In a preferred embodiment, the microplate 10 may be dipped into a container 50 containing the sample product 52, as shown in FIG. 4. As will be discussed below in the specific examples below, the microplate is held in the beaker of the sample solution for a period of time to allow the sample solution to penetrate the substrate or the membrane and therefore allow the mixing of the product sample with the light-emissive compound.

Figure 5:
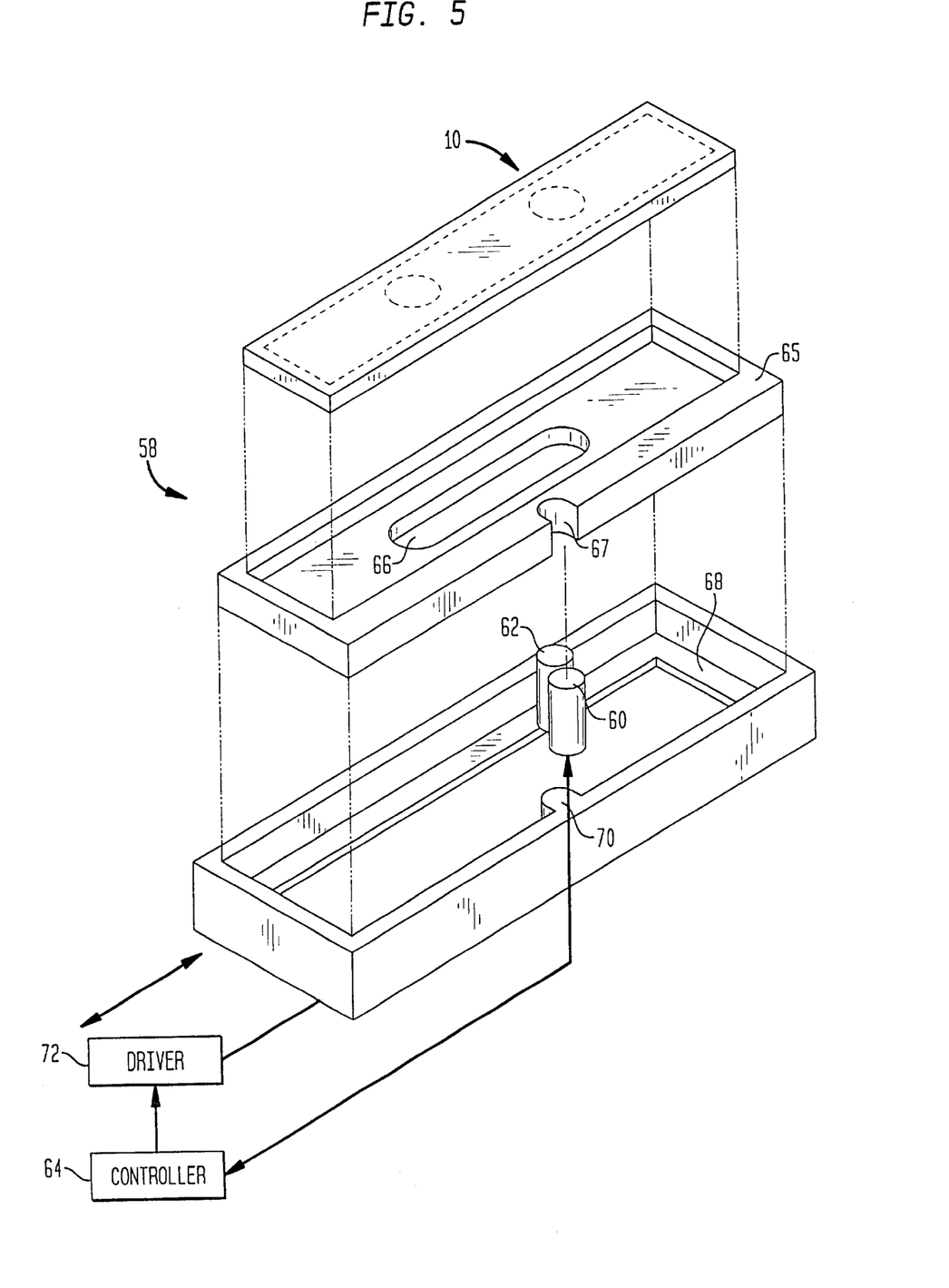
FIG. 5 is a perspective view of an apparatus used to determine product sample authenticity in combination with the authenticating compound and substrate.

Turning now to FIG. 5, a system for authenticating a product sample is described. As shown schematically in FIG. 5, the system includes a product authentication device 58 for reading the microplate. The device includes a light source 60 for irradiating the microplate with a predetermined wavelength of light. An optical detector 62, which may be coextensive with the light source, is used to detect at least one emitted wavelength of light generated by the light-emissive compound in response to the irradiated wavelength of light. This emitted wavelength of light is then used to provide a sample characteristic. A controller 64 is coupled to the optical detector 62 for receiving the sample characteristics. The controller may be coupled to a database (not shown) in which to gain access to a fingerprint representative of an authentic sample. Thus the controller may compare the received sample characteristics with the fingerprint to determine the authenticity of the sample product.

Alternatively, the fingerprint may be a previously stored sample characteristic of a known authentic sample. Thus, in one embodiment, in order to detect authenticity of a sample product, a sample of a known product is applied to the microplate containing the light-emissive compounds as described above and scanned to receive the emitted wavelength of light. This sample characteristic is stored as a fingerprint in the memory of the controller. A second microplate is prepared with a sample of unknown product and is also scanned using the device disclosed herein to obtain a sample characteristic of the unknown product sample. The unknown product sample characteristic and the fingerprint of the known sample is compared to determine whether the unknown sample is authentic.

The authentic fingerprint data or fingerprint emission profile data may be stored in the controller or stored in a remote host computer and associated database. In this regard, the controller may communicate with the host computer via data cable, for example, a modem. Of course, those skilled in the art will recognize in view of this disclosure that other communication links may be used, such as a direct data link, satellite transmission, coaxial cable transmission, fiber optic transmission or cellular or digital communication. Also, the communication link may be a direct line or through the Internet.

To facilitate holding the microplate relative to the light source and optical detector, the device 58 may further include a microplate frame 64 which is adapted to receive the microplate. Specifically, the microplate of FIG. 1 containing the sample product thereon is inverted such that the 14, 16 is facing toward an opening 66 of the frame. The optical detector and light source is able to scan through the opening of the frame to scan the macroareas 14, 16. The frame may have an indexing feature, such as a recess 67.

Further, it may be desirable in some instances to move the microplate relative to the optical detector and light source. In this regard, the device 58 may include a tray 68 that is adapted to receive the frame. The tray also includes an indexing feature, such as tab 70, to cooperate with the recess 67 on the frame 64. The device may also include a driver 72, coupled to the controller to move the tray relative to the optical detector and the light source and subsequently the frame.

It may be desirable to pre-read or pre-scan the microplate in order to obtain a base line of the emitted wavelength of the light-emissive compound without interaction with the sample product. In this case, before applying the sample product, a microplate is placed in the device and is scanned as described above. Next, the sample product is applied to the same microplate and the microplate, together with the sample product, is scanned. Thus, any variation of background reflection or fluorescence may be obviated due to the use of the base line.

In one embodiment, the portable authentication device 58 may be a table top device.

The controller may be a processor such as a PALM PILOT® or other data logger. Power to the device, of course, may be powered by batteries, such as rechargeable batteries. Although the controller may be a hand-held PALM PILOT®, a dedicated controller or a lap top or desk top computer may be used.

Also in a preferred embodiment, the light source may be provided by light-emitting diodes, such as model no. HLMP CB15, sold by Hewlett Packard, Calif., USA, which may or may not be infra red light emitting diodes. Alternatively, the light source may be a laser light source. In either case, the light sources match the excitation wavelength of the light-emissive compounds contained on the substrate. Other components may include source filters such as a band pass or cutoff filter to isolate wavelengths of light from the light source. Lenses also may be provided which focus light from the light source onto the microplate. An optical detector, such a charged couple device (CCD) may be used. An example of such a CCD is model no. H53308 sold by Edmonds Scientific, N.J., USA. An emission filter, such as a band pass or cutoff filter may be used to isolate excitation wavelengths from emissions spectra due to light emission from the microplate.

Detection of the light emitted from the light-emissive compound may be used using any imaging technique, such as infra red, near infra red, far infra red, foyer transformed infra red, ramonspectroscopy, time resolved fluorescence, fluorescence, luminescence, phosfluorescence and visible light imaging.

A change in spectroscopy, such as light emission, due to the presence of light-emissive compounds alone can be determined from the formula [(Fd−Fp)/Fd]×100 where the light-emission of the light emissive compound and the absence of the sample product is Fd, and the light emission after adding the sample product to the microplate is Fd. The light-emission changes as a result of interaction of the light-emissive compound with the sample product. The emission filters may be used to filter undesired wavelengths of light emitting from the sample and the light-emissive compounds such that, for example, only peak wavelengths of light are passed through. The light is then directed to the optical detector, which generates a voltage level indicative of the amount of light emitted.

It is to be appreciated that although a dedicated authentication device 58 is described with reference to FIG. 5, the microplates according to the present invention may be used in conjunction with any suitable imager, such as a Molecular Dynamics Fluorlmager 575. Of course any microplate reader can be used, (e.g., Cytofluor).

It is also to be appreciated that the intensity or quantity of light-emission from the sample is detected. However, according to one aspect of the invention, intensity, decay or change in the quantity of light-emission over time may be used to provide the sample characteristic. Alternatively, any such combinations may be used to provide the sample characteristic. Thus, "light-emission" means intensity or quantity or intensity, decay or change in quantity of light emitted from the sample.

Rather than, or in addition to, comparing certain spectral properties, such as light emission from the light-emissive compound to a stored fingerprint, in some instances it may be desirable to compare a ratio of light emission of two different wavelengths of light to a stored ratio fingerprint. This may be accomplished by providing a light-emissive compound that is capable of emitting two different peak wavelengths of light or, alternatively, providing two or more different light-emissive compounds, each producing a characteristic peak wavelength having a certain light emission. For example, two light-emissive compounds are applied to the substrate. An excitation wavelength is applied such that the first light-emissive compound may have a relative fluorescence unit (RFU) of 98 at a peak wavelength ($\lambda 1$) of 575 $\mu$m and the second light-emissive compound has an RFU of 76 at a peak wavelength ($\lambda 2$) of 525 $\mu$m. The ratio of the RFU values at the peak wavelengths 575 to 525 is approximately 1.3. This ratio of 1.3 may then be used in comparison to the stored fingerprint ratio. Although relative fluorescence units are used in this example to indicate the value of the amount of light emitted, other units may be used, such a photon count, for example.

It is to be appreciated that the sampling rate of the device may include about 10,000 readings. Thus, a high degree of confidence may be obtained in providing the sample characteristics.

With such a large amount of data generated, although possible, conventional data analysis comparing one or two variables at a time, is not practical. Thus, according to one aspect of the invention, multivariable analysis or multivariable padding recognition may be used. In a preferred embodiment, Tukey's analysis and Principle Component Analysis (PCA) are used. Other multivariable techniques that may be utilized include Hierarchical Cluster Analysis, K Nearest Neighbor, Pineapple Component Regression, Partial Least Squares Regression, and Soft Independent Modeling of Class Analogy (SIMCA). These multivariable techniques reduce the dimensionality of the data to two or three dimensions, allowing the pattern or relationships to be generated.

Analysis of the data may also be performed by developing plots having distinct clusters summarizing the similarity and differences among the samples being analyzed to a stored standard. Such analysis may be performed in addition to or in the alternative to the above-mentioned multivariable or multivariable pattern recognition.

Example #1

Detection of Authentic Guinness

In this example, the sample products are Guinness, Beamish and Murphy's stout. Light-emissive compounds are identified in a manner similar to that described in U.S. Pat. No. 5,753,511. For Guinness authentication, light-emissive compound #29, which is bis-(1,3-diethylthiobarbituric acid) trimethine oxonol, and light-emissive compound #18, which is Fluorescein-6-isothiocyanate, are prepared at 25 and 10 uM respectively, and transferred to a silica substrate which is available affixed to a 25×75 mm glass microscope slide. Both light-emissive compounds can be obtained from Molecular Probes, Eugene, Oreg., USA. The light-emissive compounds are dried onto the substrate. Comparison of the authentic and test samples is performed by testing them at the same location at the same time. This reduces any inaccuracies associated with differential temperature, light, or light-emissive compound concentration. A portable fluorescent reader is programmed for the appropriate emission filters (emission filters set at 570 and 535 nM for dyes 29 and 18, respectively). A first microplate is used to enter reference values for the authentic sample. This is accomplished by placing the a microplate, without any product sample thereon, in the reader. The reader measures the light emission of the light-emissive compounds (dry read). The microplate is then dipped into authentic Guinness for a period of time. The microplate is then removed and excess product sample is wiped off. The microplate is then placed back into the reader. A second reading is taken (wet read). The dry read value is divided by the wet read value to give the relative change in fluorescence. This is entered into the controller as a reference value for the authentic sample. A second microplate is dry read and wet read for use with the test sample. The relative change in fluorescence is computed. If the test sample value is different from the reference by a given percentage, then the sample fails and is suspected of being non-authentic or of poor quality.

The algorithm for deciding a pass versus fail is as follows:

calculate dry/wet value for reference (R)

calculate dry/wet value for test sample (T)

from prior testing establish a range for authentic product (typically 5–15%)

test sample fails if either T>R×1.07 or T<R×0.93 (tolerance set at 7%)

test sample passes if R×0.93≦T≦R×1.07

Results with Light-emissive Compound #29:

| Sample | Serial # | dry read divided by wet read |
|---|---|---|
| 1. Guinness, draft can | 21 D 9 G3 01:49 | 5.12 |
| 2. Beamish, draft can | 5 3 9 20 15:49 | 7.41 (F) |
| 3. Murphy's, draft can | L9096E 826 11:49 | 6.06 (F) |
| 4. Guinness Stout (repeat 1) | 21 D 9 G3 01:49 | 5.02 (P) |

(Tolerance range for Guinness at 7% is 4.76–5.47%)

Example #2

Detection of Authentic Ballantine's Finast

The following provides an example for authenticating Ballantine's Finast using microplates with light-emissive compound #149, which is available as Newport Green and can be obtained from Molecular Probes, Eugene, Oreg., USA, applied at a concentration of 20 $\mu$M and read at an emission wavelength of 550 nM. The testing was performed as described in example 1.

Portable Authentication Device Readings

| Sample | dry/wet (Pass/Fail) |
|---|---|
| Ballantine's Finast (BF) | (authentic reference) 3.76 |
| BF cut 20% with water | 2.21 (F) |
| BF cut 10% with water | 3.13 (F) |
| BF cut 20% with vodka | 2.28 (F) |
| BF cut 10% with vodka | 2.66 (F) |
| BF (repeat) | 3.72 (P) |

(Tolerance range or Ballantine's Finast at 10% is 3.38–4.14)

Example #3

Placing Aspartame Specific Dyes on a Controlled-porosity Membrane (Non-silica Surfaces)

In this example light-emissive compound samples (light-emissive compound 120) was placed on Anapore membranes (Whatman Anadisk Cat#6809-6022, United Kingdom) using a BioChip Arrayer™ from Packard Instruments (Meriden, Conn.). Small spots (less than 1000 spots/cm$^2$) can be placed on this membrane. The spot size can range from 0.1 microliters to 100 microliters. In this case an 8×7 array of spots was placed on the membrane. The spot size was approximately 1.6 mm×1.6 mm with a 250 micron spacing.

Placing the membrane with Aspartame light-emissive compound 120 in a solution of Coke Classic, the fluorescence was 5.93. Placing an exact replicate membrane with Aspartame light-emissive compound 120 in a solution of Diet Coke (containing Aspartame) the fluorescence was 15.4. The measurement was made using Fluorlmager 575 from Molecular Dynamics (Sunnyvale, Calif.).

Having thus described certain embodiments of the present invention, various alterations, modifications, and improvements will readily occur to those skilled in the art.

Such alterations, modifications, and improvements are intended to be within the scope of the invention. Accordingly, the foregoing description is by way of example only, and not intended to be limiting. The invention is limited only as defined in the following claims and the equivalents thereof.

What is claimed is:

1. A microplate comprising:
   a base;
   a porous substrate layered on said base; and
   at least one dry light-emissive compound absorbed in said substrate in a manner to allow a liquid sample placed on said microplate to permeate said substrate and thereafter react with said at least one light-emissive compound, the at least one light-emissive compound being confined to a plurality of spaced apart microareas, all located within one or more macroareas within the substrate;
   said microplate being arranged to permit radiation incident on it to interact with said at least one light emissive compound, and to permit radiation emitted by said at least one light emissive compound to exit said microplate, for analysis external of said microplate.

2. The microplate according to claim 1, wherein said substrate is formed of silica.

3. The microplate according to claim 2, wherein said silica comprises a plurality of silica particles.

4. The microplate according to claim 3 wherein each of said particles has a size less than about 25 microns.

5. The microplate according to claim 1, wherein said substrate is formed of a gel.

6. The microplate according to claim 1, wherein said substrate is a membrane.

7. The microplate according to claim 1, wherein said at least one light-emissive compound is held in said substrate without covalently bonding said at least one light-emissive compound to said substrate.

8. The microplate according to claim 1, wherein said at least one light-emissive compound enters solution when a liquid sample is placed on said microplate.

9. The microplate according to claim 1, wherein said at least one light-emissive compound comprises at least first and second light-emissive compounds, with said first light-emissive compound being interleaved with said second light-emissive compound.

10. The microplate according to claim 1, wherein said at least one light-emissive compound is disposed over a selected macroarea, with said selected macroarea comprising first and second macroareas, each comprising a different light-emissive compound.

11. The microplate according to claim 1, in combination with a system for verifying authenticity of a sample product, the system comprising:
   a product authentication device for reading said microplate, said device comprising:
      a light source for irradiating said microplate with a predetermined wavelength of light;
      an optical detector for detecting at least one emitted wavelength of light generated by the sample in response to the irradiating wavelength of light to provide a sample characteristic; and
      a controller coupled to said optical detector for receiving said sample characteristic and comparing said sample characteristic to a fingerprint.

12. The combination according to claim 11, wherein the system further comprises a frame coupled to said microplate, said frame having an indexing means for indexing said microplate relative to at least one of said light source and said optical detector.

13. The combination according to claim 12, wherein said device further comprises a tray, said tray receiving said frame.

14. The combination according to claim 13, wherein said device further comprises a driver coupled to said tray, said driver moving said tray relative to at least one of said light source and said optical detector.

15. The microplate according to claim 11, wherein said substrate is formed of silica.

16. The microplate according to claim 11, wherein said substrate is formed of a gel.

17. The microplate according to claim 11, wherein said substrate is a membrane.

18. The microplate according to claim 11, wherein said at least one light-emissive compound is held in said substrate without covalently bonding said at least one light-emissive compound to said substrate.

19. The microplate according to claim 11, wherein said at least one light-emissive compound absorbed in said substrate is dry.

20. The microplate according to claim 11, wherein said at least one light-emissive compound enters solution when a liquid sample is placed o n said microplate.

21. The microplate according to claim 11, wherein said at least one light-emissive compound comprises at least first and second light-emissive compounds, with said first light-emissive compound being interleaved with said second light-emissive compound.

22. The microplate according to claim 11, wherein said at least one light-emissive compound is disposed over a selected macroarea of said microplate, with said selected macroarea comprising a plurality of spaced apart microareas, with said at least one light-emissive compound occupying an entire microarea.

23. The microplate according to claim 11, wherein said at least one light-emissive compound is disposed over a selected macroarea with said selected macroarea comprising first and second macroareas, each comprising a different light-emissive compound.

24. The microplate according to claim 1 wherein said at least one light-emissive compound comprises a first and a second light-emissive compound, with said first light-emissive compound comprising bis-(1,3-diethylthiobarbituric acid) trimethine oxonol and with said second light-emissive compound comprising fluorescein-6-isothiocyanate.

25. A method of verifying authenticity of a sample product, the method comprising the steps of:
   providing a microplate base having at least one dry light-emissive compound disposed thereon, the microplate having a base, the base having a porous substrate layered on said base, said at least one dry light-emissive compound absorbed in said substrate;
   applying a liquid sample product to a microplate to permeate the substrate and thereafter react with the at least one light emissive compound;
   irradiating said microplate with a predetermined wavelength of light;
   detecting, external of the microplate, at least one emitted wavelength of light generated by the sample in response to the irradiating wavelength of light to provide a sample characteristic; and
   comparing said sample characteristic to a fingerprint.

26. The method according to claim 25, wherein said applying step comprises the steps of applying a known sample product to said microplate and applying an unknown sample is product to said microplate, with said known sample product providing said fingerprint.

27. The method according to claim 25, further comprising the step of first irradiating said microplate to obtain a baseline before applying the sample product to the microplate.

28. The method according to claim 25, wherein said applying step comprises the step of dipping said microplate into a sample product.

29. The method according to claim 25, wherein said applying step comprises the step of applying a liquid sample to the microplate.

30. The method according to claim 25, wherein said at least one light-emissive compound absorbed in said substrate is dry.

31. A method of verifying authenticity of a sample product, the method comprising the steps of:
   providing a microplate having a porous medium, the medium having at least 500 micropores at least some of which contain a dry light-emissive compound;
   absorbing a liquid sample into said micropores to permit the sample to solublize and interact with the light-emissive compound in the micropores;
   irradiating said microplate with a predetermined wavelength of light;
   detecting at least one emitted wavelength of light generated by the sample in response to the irradiating wavelength of light to provide a sample characteristic; and
   comparing said sample characteristic to a fingerprint.

32. The method according to claim 31, wherein said providing step comprises the step of providing said micropores on a solid base.

33. The method according to claim 32, wherein said base is flat.

34. The method according to claim 31, wherein said providing step comprises the step of forming said micropores with silica particles.

* * * * *